United States Patent [19]
Frantzen

[11] Patent Number: 6,083,259
[45] Date of Patent: Jul. 4, 2000

[54] AXIALLY NON-CONTRACTING FLEXIBLE RADIALLY EXPANDABLE STENT

[76] Inventor: John J. Frantzen, 424 Poker Flat Rd., Copperopolis, Calif. 95228

[21] Appl. No.: 09/192,803

[22] Filed: Nov. 16, 1998

[51] Int. Cl.[7] .................................................. A61F 2/06
[52] U.S. Cl. .......................................... 623/1.15; 623/1.17
[58] Field of Search .......................... 623/1, 12; 606/198, 606/191, 194, 195

[56] References Cited

U.S. PATENT DOCUMENTS

| | | |
|---|---|---|
| D. 380,266 | 6/1997 | Boatman et al. . |
| D. 380,831 | 7/1997 | Kavteladze et al. . |
| 4,704,126 | 11/1987 | Baswell et al. . |
| 4,858,264 | 8/1989 | Reinhart . |
| 4,936,057 | 6/1990 | Rhoades . |
| 5,104,404 | 4/1992 | Wolff . |
| 5,108,417 | 4/1992 | Sawyer . |
| 5,133,732 | 7/1992 | Wiktor . |
| 5,139,480 | 8/1992 | Hickle et al. . |
| 5,195,984 | 3/1993 | Schatz . |
| 5,199,226 | 4/1993 | Rose . |
| 5,242,399 | 9/1993 | Lau et al. . |
| 5,314,444 | 5/1994 | Gianturco . |
| 5,383,892 | 1/1995 | Cardon et al. . |
| 5,421,955 | 6/1995 | Lau et al. . |
| 5,423,849 | 6/1995 | Engelson et al. . |
| 5,425,739 | 6/1995 | Jessen . |
| 5,441,515 | 8/1995 | Khosravi et al. . |
| 5,443,477 | 8/1995 | Marin et al. . |
| 5,443,496 | 8/1995 | Schwartz et al. . |
| 5,449,373 | 9/1995 | Pinchasik et al. . |
| 5,485,667 | 1/1996 | Kleshinski . |
| 5,494,029 | 2/1996 | Lane et al. . |
| 5,496,277 | 3/1996 | Termin et al. . |
| 5,507,767 | 4/1996 | Maeda et al. . |
| 5,507,771 | 4/1996 | Gianturco . |
| 5,514,154 | 5/1996 | Lau et al. . |
| 5,522,882 | 6/1996 | Gaterud et al. . |
| 5,531,741 | 7/1996 | Barbacci . |
| 5,545,210 | 8/1996 | Hess et al. . |
| 5,549,662 | 8/1996 | Fordenbacher . |
| 5,549,663 | 8/1996 | Cottone . |
| 5,554,181 | 9/1996 | Das . |

(List continued on next page.)

FOREIGN PATENT DOCUMENTS 95302708  4/1995  European Pat. Off. .

OTHER PUBLICATIONS

Patrick W. Serruys and Michael JB Kutryk, Handbook of Coronary Stents, 1998, pp. 45, 55, 78, 103, 112, 132, 158, 174, 185, 190, 207, 215, 230, 239, Second Edition, Martin Dunitz, United Kingdom.

*Primary Examiner*—Michael J. Milano
*Assistant Examiner*—Choon P. Koh
*Attorney, Agent, or Firm*—Heisler & Associates

[57] ABSTRACT

A radially expandable surgical stent 10 is provided for implantation into a body lumen. The stent 10 includes a series of circumferential elements 20 circumscribing a central axis 4 of the stent 10 and axially spaced from each other by gaps 40. Each circumferential element 20 includes a wave-like series of bends 30. Each bend 30 has one side defining a trough 32 in and an opposite side defining a crest 36. The trough 32 is that side of the bend 30 most distant from adjacent circumferential elements 20. The crest 36 is that side of each bend 30 closest to adjacent circumferential elements 20. Axial elements 50 span each gap 40 with ends of each axial element 50 attaching to circumferential elements 20 at troughs 32. Some of the axial elements 50 are configured as tie bars 51 extending linearly axially between adjacent circumferential elements 20. Other axial elements 50 can be configured as double bend links 60 extending between adjacent circumferential elements 20. The double bend links 60 include a first curve 65 and a second curve 67 which can each have their radii of curvature adjusted to allow the double bend link 60 to be expanded or compressed and allowing the stent 10 to flex with the central axis 4 bending. The stent 10 can additionally include enhanced density markers 360 which increase the visibility of portions of the stent 10 when viewed with a medical imaging device.

11 Claims, 5 Drawing Sheets

U.S. PATENT DOCUMENTS

| | | |
|---|---|---|
| 5,562,641 | 10/1996 | Flomenblit et al. . |
| 5,562,728 | 10/1996 | Lazarus et al. . |
| 5,569,295 | 10/1996 | Lam . |
| 5,578,149 | 11/1996 | DeScheerder et al. . |
| 5,591,195 | 1/1997 | Taheri et al. . |
| 5,591,197 | 1/1997 | Orth et al. . |
| 5,591,223 | 1/1997 | Lock et al. . |
| 5,591,226 | 1/1997 | Trerotola et al. . |
| 5,591,230 | 1/1997 | Horn et al. . |
| 5,603,721 | 2/1997 | Lau et al. . |
| 5,605,530 | 2/1997 | Fischell et al. . |
| 5,607,442 | 3/1997 | Fischell et al. . |
| 5,607,445 | 3/1997 | Summers . |
| 5,618,299 | 4/1997 | Khosravi et al. . |
| 5,624,411 | 4/1997 | Tuch . |
| 5,630,840 | 5/1997 | Mayer . |
| 5,632,760 | 5/1997 | Sheiban et al. . |
| 5,632,763 | 5/1997 | Glastra . |
| 5,632,771 | 5/1997 | Boatman et al. . |
| 5,634,941 | 6/1997 | Winston et al. . |
| 5,636,641 | 6/1997 | Fariabi . |
| 5,637,113 | 6/1997 | Tartaglia et al. . |
| 5,697,971 | 12/1997 | Fischell et al. . |
| 5,718,713 | 2/1998 | Frantzen . |
| 5,741,327 | 4/1998 | Frantzen . |
| 5,746,691 | 5/1998 | Frantzen . |
| 5,843,175 | 12/1998 | Frantzen . |

AXIALLY NON-CONTRACTING FLEXIBLE RADIALLY EXPANDABLE STENT

FIELD OF THE INVENTION

The following invention relates to surgical stents which are implanted within a body lumen while in a first compressed configuration and then can be radially expanded to a second expanded configuration. More specifically, this invention relates to surgical stents which resist axial contraction when radially expanded and which exhibit desirable flexibility characteristics before radial expansion.

BACKGROUND OF THE INVENTION

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the catheter has been removed.

Radially expandable stents come in a variety of different configurations to provide optimal performance to various different particular circumstances. For instance, the patents to Lau (U.S. Pat. Nos. 5,514,154, 5,421,955, and 5,242,399), Baracci (U.S. Pat. No. 5,531,741), Frantzen (U.S. Pat. Nos. 5,718,713, 5,741,327, 5,746,691), Gaterud (U.S. Pat. No. 5,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (Patent No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662), and Wiktor (U.S. Pat. No. 5,133,732), each include some form of radially expandable stent for implantation into a body lumen. Other prior art stents are compiled in the Handbook of Coronary Stents, Second Edition, produced by the Rotterdam Thoraxcenter Interventional Cardiology Group.

Most of these prior art stents suffer from undesirable axial contraction when radially expanded. Stents can be made to resist axial contraction upon radial expansion by including axial elements therein extending continuously from a first end of the stent to a second end of the stent. However, such continuous axial elements tend to make the stent stiff and exhibit less flexibility characteristics than needed to allow the stent to be easily passed through tortuous arterial pathways or other tightly curving body lumens effectively. Some of these prior art stents, such as the stents described in the patents to Frantzen resist axial contraction upon radial expansion by locating axial elements offset from each other and within troughs of adjacent circumferential elements. While flexibility does improve somewhat by offsetting such axial elements, additional flexibility is often needed.

It is known to provide a combination of trough-to-trough axial elements alternating with curved axial elements oriented in a crest-to-crest fashion, such as with the stents described in the patents to Frantzen. The trough-to-trough axial elements resist axial contraction upon radial expansion of the stent and the crest-to-crest axial elements are curved to allow for some flexibility in the stent. Because the flexible axial elements extend crest-to-crest, these elements do not resist axial contraction of the stent upon radial expansion, but rather rely on the trough-to-trough axial elements. Accordingly, a need exists for a surgical stent which includes axial elements which both extend in a trough-to-trough fashion and also include flexibility characteristics in a single axial element.

Prior art stents have additionally suffered from poor visibility when viewed with a medical imaging device, such as a fluoroscope. During surgery, a surgeon will typically view the stent positioning procedure with a fluoroscope or other imaging device. Stents made from stainless steel, while adequate in most respects, are particularly difficult to view because they do not appear with a high degree of contrast relative to adjacent body tissues when viewed with a fluoroscope or other medical imaging device. This poor radiopacity is due partially to the particular radiopacity characteristics of stainless steel and also to the geometric configuration of the stent. Typical prior art stents are made from thin elements or wires with a significant amount of open space there between. Hence, a relatively small amount of stent material is present for a given area and this low density of stent material tends to decrease the radiopacity of the stent.

Known prior art methods for enhancing the radiopacity of a surgical stent include plating at least portions of the stent with chemical elements having a higher radiopacity or adding additional structural elements to the stent which are formed of a radiopaque chemical element so that the structural elements will be more visible. These prior art radiopacity enhancing techniques are inadequate due to the complexity involved in attaching or plating radiopaque material to the stent. Additionally, unless a proper amount of radiopaque material is added to the stent, the stent can return too strong of an image on the fluoroscope or other medical imaging device, causing the stent to obscure adjacent bodily tissues and decrease the surgeon's ability to properly locate the stent. Accordingly, a need exists for a simple way to add a radiopaque marker to a stent which enhances the radiopacity of portions of the stent just enough for clear viewing with a medical imaging device.

SUMMARY OF THE INVENTION

The stent of this invention is configured to resist axial contraction when radially expanded from a first collapsed diameter to a second expanded diameter. Additionally, the stent of this invention is configured to maximize flexibility characteristics of the stent before radial expansion thereof to allow the stent to be passed reliably through tortuous arterial pathways.

The stent generally includes a series of circumferential elements circumscribing a central axis and oriented in separate planes spaced axially from each other. Each circumferential element includes a wave-like series of bends. Each bend includes a trough and a crest. The crest is defined as that portion of each bend which is closest to the adjacent circumferential element that the crest faces. The trough is that portion of each bend which is most distant from the adjacent circumferential element that the trough faces. In essence, each location on the bend is both part of a crest and part of a trough depending on what side of that portion of the bend is being examined.

Axial elements are provided in the form of flexible links which span gaps between adjacent circumferential elements and attach to adjacent circumferential elements at troughs thereof. These flexible links additionally include at least one curve which can have a radius of curvature thereof altered so that the flexible link can adjust in length axially. When the flexible link is allowed to adjust in length axially, the stent is allowed to flex in a manner causing a central axis of the stent to bend. By locating these flexible links in a trough-to-trough orientation spanning gaps between adjacent circumferential elements, the flexible links additionally hold the adjacent circumferential elements apart and resist axial contraction of the stent when the stent is radially expanded.

The stent can additionally include other axial elements such as linear tie bars spanning some of the gaps, depending upon the particular flexibility needs of the stent. The tie bars extend trough-to-trough like the flexible links so that the axial length of the stent is maintained upon radial expansion.

While the flexible link can take on various different configurations, the flexible link is preferably configured as a double bend link which includes a first tip and a second tip at opposite ends of the double bend link joined to troughs of circumferential elements on opposite sides of the gap spanned by the double bend link. A first curve and a second curve are interposed on the double bend link between the first tip and the second tip. Legs space the curves from each other and from the tips. Each of the curves can have a radius of curvature thereof altered so that the double bend link can flexibly adjust in length axially, facilitating flexing of the entire stent.

If enhanced radiopacity is desirable to allow the surgeon to more easily view the exact location of the stent when utilizing an imaging device, an enhanced density marker can be located on the stent such as at ends of the stent and/or at a midpoint of the stent. Such a marker includes additional in-phase elements of the same material as other parts of the stent located directly adjacent circumferential elements at the location where the marker is desired. The additional elements enhance a density of stent material adjacent the existing circumferential element so that that portion of the stent becomes more visible when viewed through a medical imaging device.

OBJECTS OF THE INVENTION

Accordingly, a primary object of the present invention is to provide a radially expandable surgical stent which does not contract axially when expanded radially.

Another object of the present invention is to provide a surgical stent which is sufficiently flexible to allow the stent to be passed through tortuous arterial pathways so that a maximum number of implantation sites for the stent can be effectively reached without damaging the stent or the patient.

Another object of the present invention is to provide a surgical stent which features axial elements which resist contraction axially when the stent is expanded radially and enhance flexibility of the stent in a single element.

Another object of the present invention is to provide a surgical stent which includes additional elements at locations where enhanced visibility of the stent is desired when the stent is viewed through a medical imaging device.

Another object of the present invention is to provide a surgical stent which can be reliably manufactured in a manner similar to that of other prior art surgical stents.

Another object of the present invention is to provide a surgical stent which can be implanted with known stent delivery tools using known stent delivery techniques.

Another object of the present invention is to provide a surgical stent which can be reliably flexed and expanded radially without fracture of individual elements of the stent.

Other further objects of the present invention will become apparent from a careful review of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 is directed to a surgical stent which beneficially combines flexibility attributes with a resistance to axial contraction when radially expanded. The stent 10 has a first compressed diameter (FIG. 1) and a second expanded diameter (FIG. 2). The stent 10 is sufficiently flexible when in the compressed configuration to allow the stent 10 to flexibly pass through body lumens having curves with a small radius of curvature, to maximize a number of sites at which the stent 10 can be implanted.

Figure 1:
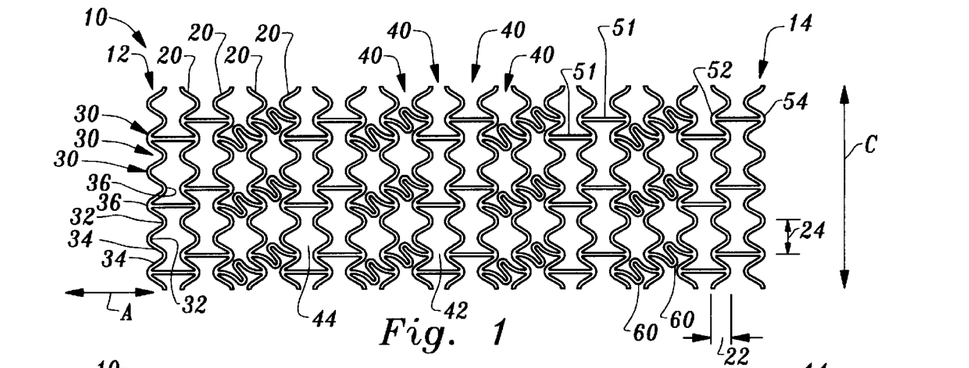
FIG. 1 is a cylindrical projection of a stent according to a preferred embodiment of this invention, before radial expansion thereof.
Figure 2:
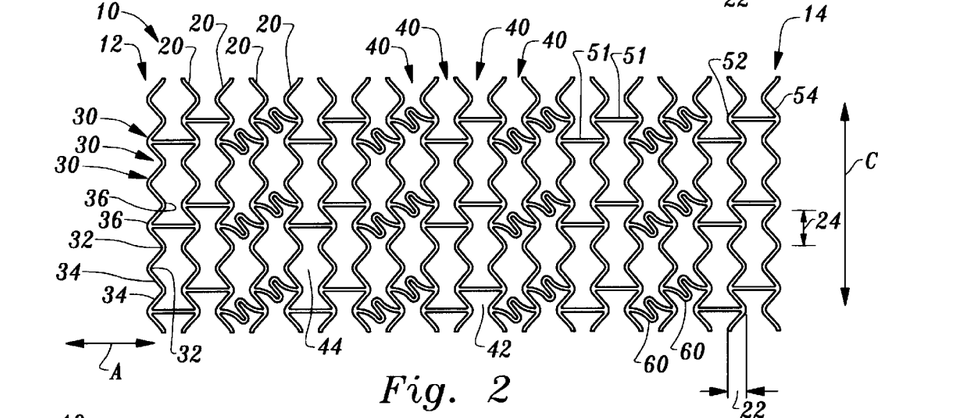
FIG. 2 is a cylindrical projection of that which is shown in FIG. 3, after partial radial expansion thereof.

In essence, and with particular reference to FIGS. 1–5, the primary features of the surgical stent 10 are described. The stent 10 includes a series of circumferential elements 20 circumscribing a central axis 4 (FIGS. 4 and 5) of the stent 10 and located in separate planes spaced axially from each other by gaps 40. Each circumferential element 20 is configured with a wave-like series of bends 30 therein (FIG. 1). Each bend 30 defines either a trough 32 or a crest 36 depending on the direction from which the bend 30 is viewed. The trough 32 defines a portion of each bend 30 which is most distant from adjacent circumferential elements 20 that the trough 32 faces. The crest 36 defines a portion of each bend 30 which is closest to adjacent circumferential elements 20 which the crest 36 faces.

Each gap 40 is spanned by at least one axial element 50. The axial elements 50 are either tie bars 51 or double bend links 60. The tie bars 51 extend linearly between troughs 32 on opposite sides of the gap 40 spanned by the tie bar 51. The double bend links 60 also extend in a trough 32 to trough 32 manner between circumferential elements 20 adjacent the gap 40 spanned by the double bend links 60. The double bend links 60 additionally include curves 65, 67 which can adjust their curvature to allow the double bend links 60 to adjust in length axially and give flexibility to the stent 10.

More specifically, and with particular reference to FIGS. 1–5, the details of the configuration of the preferred embodiment of the surgical stent 10 are described. The contour of the stent 10 is generally outlined by the series of circumferential elements 20 circumscribing the central axis 4 (FIGS. 1 and 2) of the stent 10. Each circumferential element 20 includes a wave-like series of bends 30. Portions of each bend 30 which are most distant from adjacent circumferential elements 20 define troughs 32. Portions of each bend 30 which are closest to adjacent circumferential elements 20 define crests 36. A midway point between each trough 32 and crest 36, where a curvature of the bend 30 changes, defines an inflection point 34. Specifically, each trough 32 actually defines a region between adjacent inflection points 34 which is most distant from the adjacent circumferential element 20 and the crest 36 defines a region between adjacent inflection points 34 which are closest to the adjacent circumferential element 20.

Whether a portion of the bend 30 is a trough 32 or a crest 36 is a matter of perspective depending on what side of the bend 30 is being viewed. One side of a bend 30 defines a crest 36 closest to an adjacent circumferential element 20 and the other side of the bend 30 defines a trough 32 most distant from an adjacent circumferential element 20.

The dimensions of the bends 30 forming each circumferential element 20 can be quantified with reference to an amplitude 22 (FIGS. 1–3) and a wave length 24. The actual measurements for the amplitudes 22 and wave lengths 24 for the stent 10 can vary depending on the particular application for which the surgical stent 10 is configured. Also, the amplitudes can vary between circumferential elements 20 so that the stent 10 can taper in a non-cylindrical fashion between a first end 12 and a second end 14 of the stent 10. As the stent 10 is radially expanded, along arrow R (FIGS. 1 and 2) the amplitude 22 will decrease in size and the wave length 24 will increase. The increase in wave length 24 will increase a circumferential size of the stent 10 (arrow C of FIGS. 1–3), allowing the stent 10 to expand radially and yet still maintain the circumferential elements 20 in a configuration completely circumscribing the central axis 4 (FIGS. 1 and 2) of the stent 10.

Because the amplitude 22 decreases when the stent 10 is radially expanded, the stent 10 has a natural tendency to contract axially, along arrow A, when the stent 10 is radially expanded. However, because this stent 10 has circumferential elements 20 joined together with axial elements 50 which connect at troughs 32 in the circumferential elements 20, this axial contracting tendency is nullified or slightly reversed by this stent 10.

The stent 10 is preferably made from stainless steel or other bio-compatible materials. The stent 10 is configured so that structures forming the stent 10, including the elements 20, 50 can bend somewhat without breaking, to facilitate radial expansion of the stent 10. Alternatively, the stent 10 can be made from nickel titanium alloys which are both bio-compatible and have an ability to change shape and radially expand when transforming between austenite and martensite solid phases.

The axial elements 50 can either be configured as tie bars 51 or as double bend links 60. The tie bars 51 are substantially linear between a first junction 52 where the tie bar 51 attaches to one circumferential element 20 and a second junction 54 where the tie bar 51 attaches to another circumferential element 20 on an opposite side of the gap 40. Because the tie bars 51 are aligned axially, when axial forces are exerted on the tie bars 51 (in either a compression or tension fashion), such as when the stent 10 is trying to flex with the central axis 4 curving, the tie bars 51 resist such axial forces. This tendency of tie bars 51 to resist axial forces is beneficial when a stent 10 of greater strength, particularly in an axial direction, is desirable. This attribute of tie bars 51 is disadvantageous when enhanced flexibility for the stent 10 is desired.

Preferably, the tie bars 51 do not span each gap 40 between circumferential elements 20 in the stent 10. Rather, at least some of the gaps 40 are spanned by the double bend links 60. Most preferably, a set of three tie bars 51 span a gap 40 directly adjacent to the first end 12 of the stent 10 and set of three tie bars 51 span the next gap 40 which is spaced one gap 40 away from the first end 12. Preferably, a third gap 40 and a fourth gap 40 from the first end 12 are spanned by the double bend links 60, in sets of three double bend links 60, spanning both the third gap 40 and the fourth gap 40 from the first end 12. A fifth gap 40 from the first end 12 is preferably spanned by tie bars 51. This pattern of pairs of gaps 40 spanned by similar axial elements 50 preferably continues from the first end 12 to the second end 14 of the stent 10 with tie bars 51 beginning and ending the pattern of axial elements 50. In this way, a rather uniform distribution of strength and flexibility is dispersed from the first end 12 to the second end 14 of the stent 10. While not preferred, it is conceivable that a single gap 40 could be spanned by a combination of both tie bars 51 and double bend links 60.

Preferably, each circumferential element 20 is out of phase with adjacent circumferential elements 20 so that the gaps 40 do not have a uniform width. Rather, the gaps 40 have a series of minimums 42 and maximums 44. The minimums 42 define portions of each gap 40 between crests 36 of adjacent circumferential elements 20. The maximums 44 define portions of each gap 40 adjacent troughs 32 of adjacent circumferential elements 20. Preferably, both the tie bars 51 and the double bend links 60 span the gaps 40 at maximums 44 in the gap 40. Because the circumferential elements 20 are out of phase with each other, the maximums in adjacent gaps 40 are not axially aligned, but rather are offset somewhat circumferentially (along arrow C).

Figure 3:
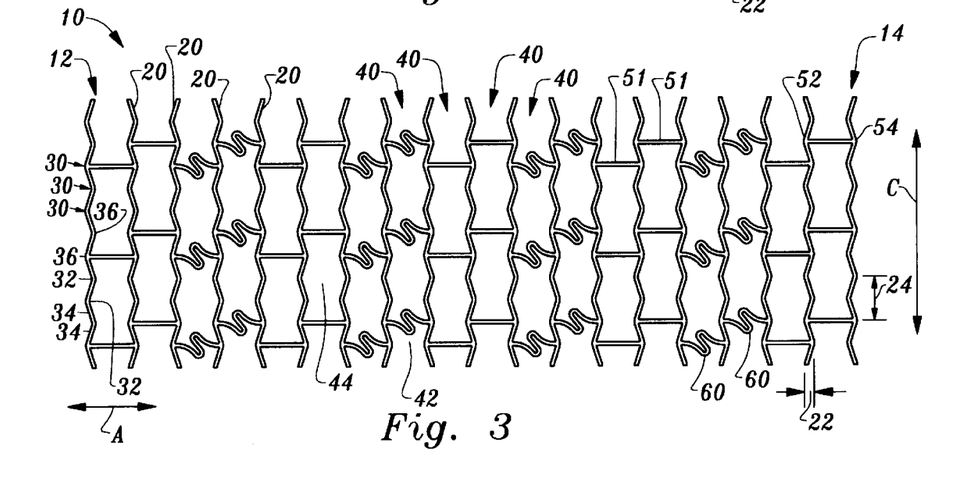
FIG. 3 is a cylindrical projection of that which is shown in FIG. 3, after full radial expansion thereof.

It will be noticed from a careful review of FIG. 3 that the circumferential elements 20 are radially expanded to a point where the circumferential elements 20 are nearly circular in shape and have been radially expanded fully. Most prior art stents do not radially expand fully and hence cannot be radially expanded as much as the stent 10. While full radial expansion is not required to provide the stent 10 with the benefits disclosed herein, full radial expansion beneficially allows the surgeon to select a stent having a desired maximum radial expansion and then use a balloon expansion catheter or other expansion device for exerting a radial force on the stent 10 which does not need to be perfectly matched to the amount of radial expansion desired.

Specifically, many prior art stents must be delivered with a balloon catheter which can only expand a predefined amount radially and so the balloon catheter and the stent 10 must be carefully matched together in configuration. With a fully expanded stent 10, as shown in FIG. 3, a balloon catheter which is capable of expanding the stent beyond the fully expanded diameter can be used and when the circumferential elements 20 are fully expanded, the stent 10 will restrain the balloon from further expanding and the stent 10 will have been radially expanded the precise amount desired. This is particularly advantageous where the stent has circumferential elements which have different diameters after radial expansion so that the stent 10 has a non-cylindrical contour, in that it allows a balloon catheter which is oversized to fully radially expand each of the circumferential elements 20 forming the stent 10. The surgeon need merely ensure that a pressure exerted by the balloon catheter does not exceed the ability of the circumferential elements 20 of the stent 10 to resist so that the circumferential elements 20 are not broken by forces exerted by the balloon catheter or other radial expansion device.

When the stent 10 is configured with axial elements 50 (FIGS. 4 and 5) oriented in a trough 32 to trough 32 arrangement, and when the stent 10 is fully expanded radially (FIG. 3) the axial elements 50, whether tie bars 51 or double bend links 60, will actually tend to cause the stent 10 to elongate axially along arrow A (FIG. 3). This elongation may be desirable for certain medical situations and so would utilize a stent 10 such as that shown in FIGS. 1–3 to provide such elongation. Typically, however, such elongation would not be desirable. Elongation of the stent 10 can be minimized through the use of the double bend links 60 which can shrink axially and the overall length of the stent 10 can remain relatively constant, even when fully radially expanded.

Preferably however, to eliminate elongation of the stent 10 upon full radial expansion, the circumferential elements 20 are configured so that their bends 30 have approximately 30% greater length between adjacent bends 30 then as shown in FIGS. 1–3. The amplitude 22 of the circumferential elements 20 would remain the same. Hence,the bends 30 and the circumferential elements 20 would have a more bulbous contour. Specifically, the circumferential elements 20 adjacent the inflection points 34 would be oriented closer to an axial orientation than is shown in FIG. 1 before radial expansion of the stent 10, or actually oriented beyond an axial orientation. Using these modification techniques, the stent 10 can be modified so that it does not elongate axially, even when fully expanded radially.

Figure 6:
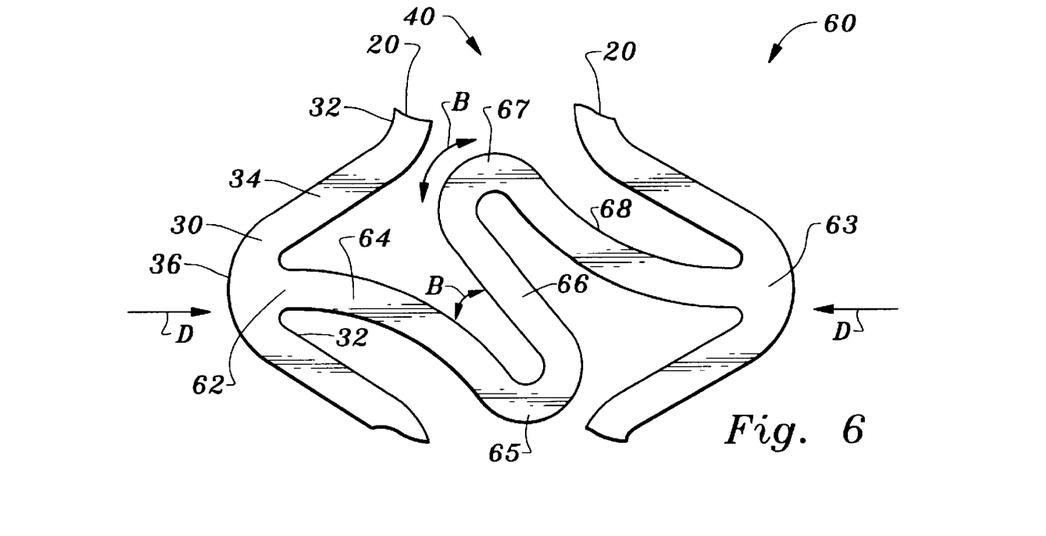
FIG. 6 is a detail of a portion of that which is shown in FIG. 1 revealing details of a double bend link of this invention.

With particular reference to FIG. 6, particular details of the double bend links 60 are described. Each double bend link 60 includes a first tip 62 which attaches to a trough 32 of one circumferential element 20 on one side of a gap 40 spanned by the double bend link 60, and a second tip 63 which attaches to a second circumferential element 20 on an opposite side of the gap 40. A first leg 64 extends from the first tip 62 to a first curve 65. The first curve 65 arcs through approximately 180° and then transitions into a second leg 66. The second leg 66 extends from the first curve 65 to a second curve 67. The second curve 67 arcs through approximately 180° and then transitions into a third leg 68. The third leg 68 extends from the second curve 67 to the second tip 63.

The first leg 64 is preferably oriented substantially axially, parallel to arrow A (FIG. 1), where said first leg 64 is adjacent the first tip 62. As the first leg 64 extends away from the first tip 62, the first leg 64 preferably curves slightly so that an end of the first leg 64 opposite the first tip 62 is skewed approximately 45° away from an axial orientation. The first leg 64 then transitions into the first curve 65 which curves approximately 180° and then transitions into the second leg 66. The second leg 66 is skewed approximately 45° with respect to arrow A and extends substantially linearly from the first curve 65 to the second curve 67. The second curve 67 is a mirror image of the first curve 65 and curves approximately 180° before the second curve 67 transitions into the third leg 68. The third leg 68 is a mirror image of the first leg 64 so that the third leg 68 begins in an orientation skewed with respect to an axial orientation but curves slightly so that the third leg 68 is oriented essentially axially where the third leg 68 transitions with the second tip 63.

The first curve 65 and second curve 67 can each flex somewhat so that a radius of curvature of the curves 65, 67 can be modified. This flexing of the curves 65, 67 is illustrated by flex arrows B (FIG. 6). When axially compressive forces (along arrow D of FIG. 6) are exerted on the double bend link 60, the radius of curvature of the curves 65, 67 will tend to decrease and the legs 64, 66, 68 will tend to be oriented closer to each other and more closely aligned with an axial direction defined by arrow A (FIGS. 1–5). When an axially expanding load, in a direction opposite to that shown by arrow D, is exerted on the double bend link 60, the curves 65, 67 will tend to have their radii of curvature increased and the legs 64, 66, 68, and especially the second leg 66, will tend to rotate away from an axial orientation. The portions of the double bend links 60 closest to the circumferential elements 20 are narrow enough to fit into troughs 32 of the circumferential elements 20 both before and after radial expansion of the stent 10.

Figures 4, 5:
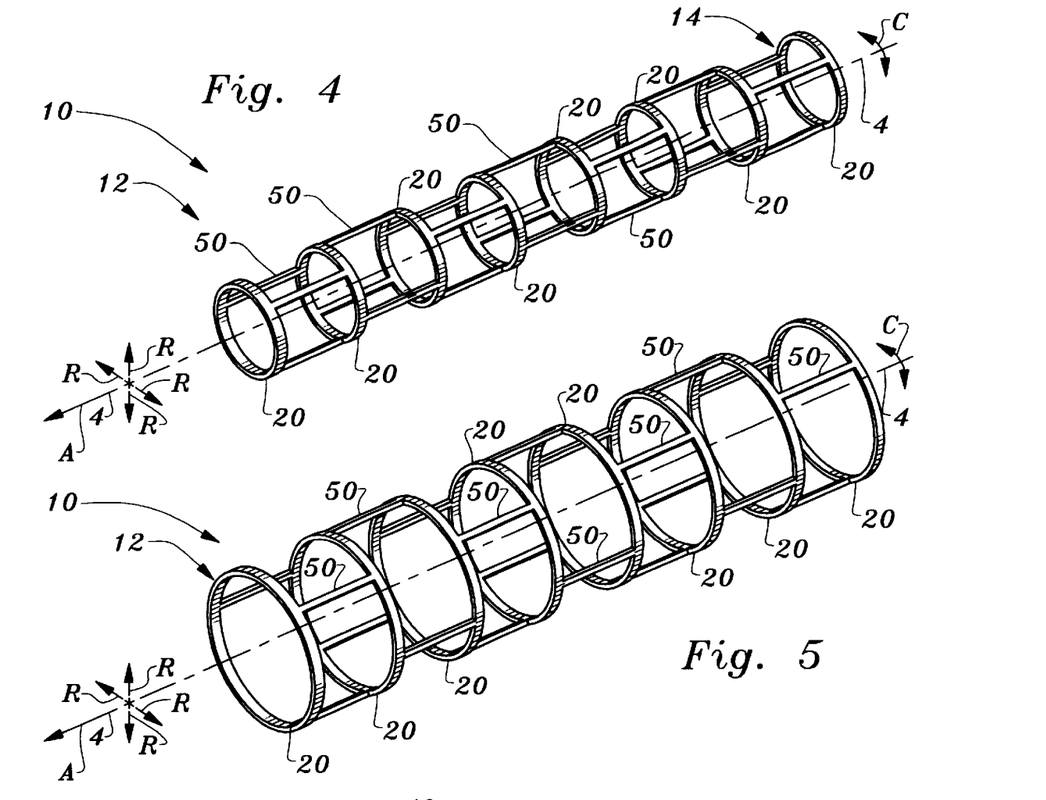
FIG. 4 is a perspective view of the stent of this invention before radial expansion. For simplicity in this figure, circumferential elements are merely shown as being circular and axial elements are merely shown as being linear. In fact, the circumferential elements and axial elements are preferably configured as shown in FIGS. 1–3.
FIG. 5 is a perspective view of that which is shown in FIG. 4 after radial expansion.

Axial forces can be exerted on the double bend links 60 at two different times during implantation of the surgical stent 10. Initially, when the stent 10 is in a first compressed configuration and is being passed through tortuous arterial pathways, such as those of many coronary arteries where stent 10 implantation may be desired, the stent 10 will be caused to flex in a manner bending the central axis 4 (FIGS. 4 and 5). When the stent 10 desires to flex, the individual double bend links 60 will be extended on a portion of the stent 10 located outside of the curve of the stent 10 and will tend to be compressed on a portion of the stent 10 inside of the curve formed by the stent 10. The double bend links 60 preferably are compressed axially in length somewhat on an inside portion of the stent 10 and expanded axially somewhat on an outside portion of the stent 10. The ability of the double bend links 60 to both expand and contract axially increases an overall flexibility provided to the stent 10 by the double bend links 60 when compared to many prior art stents which have flexible links which only allow expansion rather than both expansion and contraction.

Second, after the stent 10 has been located where desired, the stent 10 is radially expanded. During the radial expansion process, each circumferential element 20 is transformed in a manner decreasing the amplitude 22 and increasing the wave length 24 of the circumferential element 20. When this transformation occurs, the stent 10 has an overall tendency to contract axially. Countering this axially contracting tendency may be tie bars 51 which are oriented at maximums 45 in the gaps 40 and which are tending to elongate the stent 10 axially upon radial expansion. Hence, during this radial expansion of the stent 10 various different axial forces, especially compressive forces, may be exerted upon the double bend links 60. The ability of the double bend links 60 to be compressed somewhat beneficially allows the stent 10 to be radially expanded in a manner which avoids damage to the stent 10 or damage to the lumen in which the stent 10 is being radially expanded. These attributes of the double bend link 60 which cause it to enhance a flexibility of the stent 10 can cause the double bend link 60 to be referred to as a flexible link. The double bend link 60 actually does have curves 65, 67 thereof which flex when the double bend link 60 is axially extending or contracting so that the stent 10 can flex. The double bend link 60 thus provides one form of a means to adjust an axial length of the stent 10.

Figure 7:
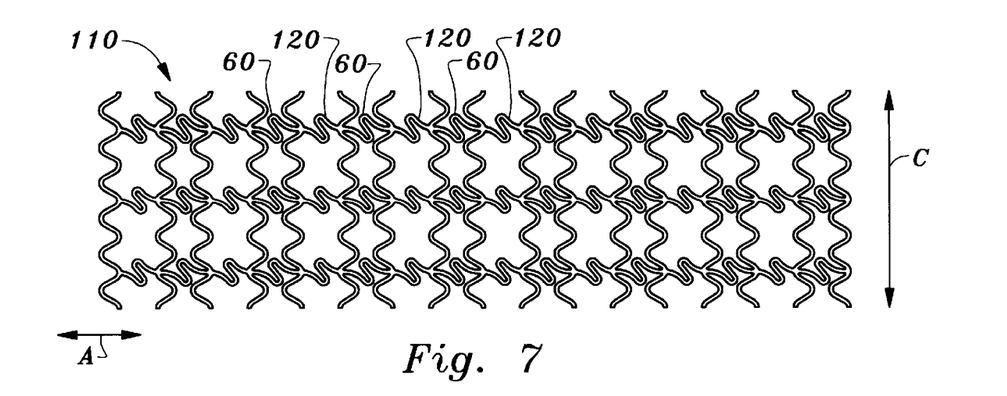
FIG. 7 is a cylindrical projection of an alternative embodiment of that which is shown in FIG. 1, exhibiting a slightly different arrangement of axial elements, before radial expansion thereof.
Figure 8:
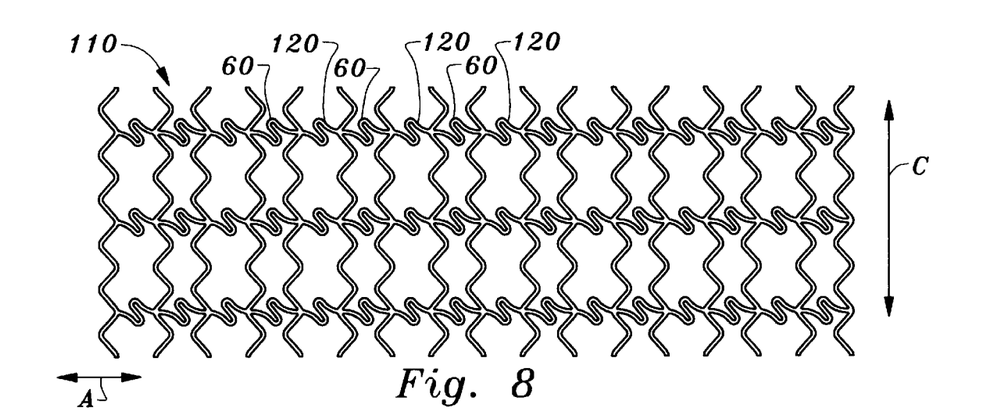
FIG. 8 is a cylindrical projection of that which is shown in FIG. 7, after partial radial expansion thereof.
Figure 9:
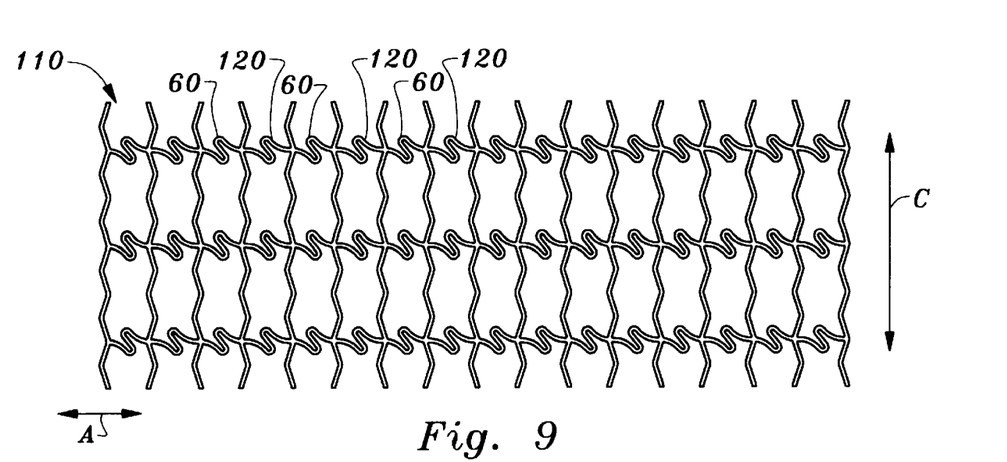
FIG. 9 is a cylindrical projection of that which is shown in FIG. 7, after full radial expansion thereof.

With particular reference to FIGS. 7–11, details of various alternative embodiments of the stent 10 of this invention are described. FIGS. 7–9 show a stent 110 which includes only trough-to-trough double bend links 60 and crest-to-crest double bend links 120. This stent 110 has the links 60, 120 aligned axially with each other. Alternatively, the links 60, 120 could be offset from each other but still feature at least some gaps spanned by the crest-to-crest double bend links 120. FIG. 7 shows the stent 110 before radial expansion. FIG. 8 shows the stent 110 after partial radial expansion. FIG. 9 shows the stent 110 after full radial expansion. Because some of the double bend links 120 extend in a crest-to-crest fashion, axial elongation along arrow A does not occur when the stent 110 is radially expanded.

Figure 10:
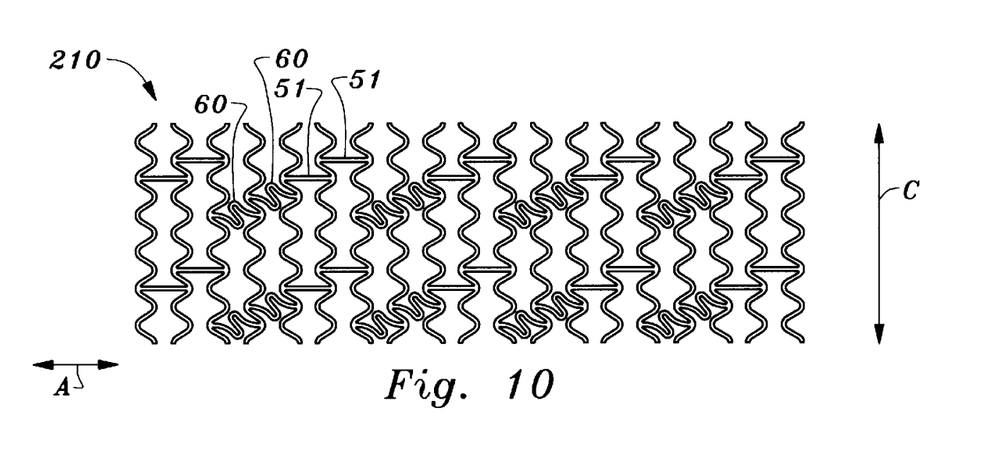
FIG. 10 is a cylindrical projection of another alternative embodiment of that which is shown in FIG. 1 with a slightly different arrangement of axial elements.

FIG. 10 shows a stent 210 featuring two axial elements spanning each gap. As with the preferred embodiment, some gaps are spanned by tie bars 51 and other gaps are spanned by double bend links 60. By providing fewer axial elements spanning each gap, an overall strength of the stent 210 is decreased, but an overall flexibility of the stent 210 is increased.

Figure 11:
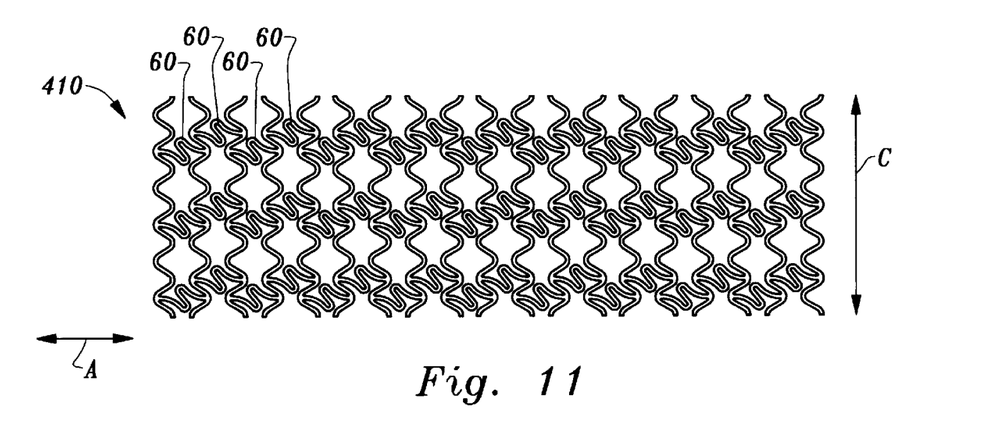
FIG. 11 is a cylindrical projection of another alternative embodiment of that which is shown in FIG. 1 with a slightly different arrangement of axial elements.

FIG. 11 shows a stent 410 similar to the stent 10 of the preferred embodiment except that each of the tie bars 51 of the stent 10 of the preferred embodiment have been replaced with double bend links 60, so that only double bend links 60 attach circumferential elements together in the stent 410. In the stent 410, both the flexibility attributes and the resistance to axial contraction upon radial expansion attributes are provided by the double bend links 60. The stent 410 provides a uniform profile of strength and flexibility characteristics.

Figure 12:
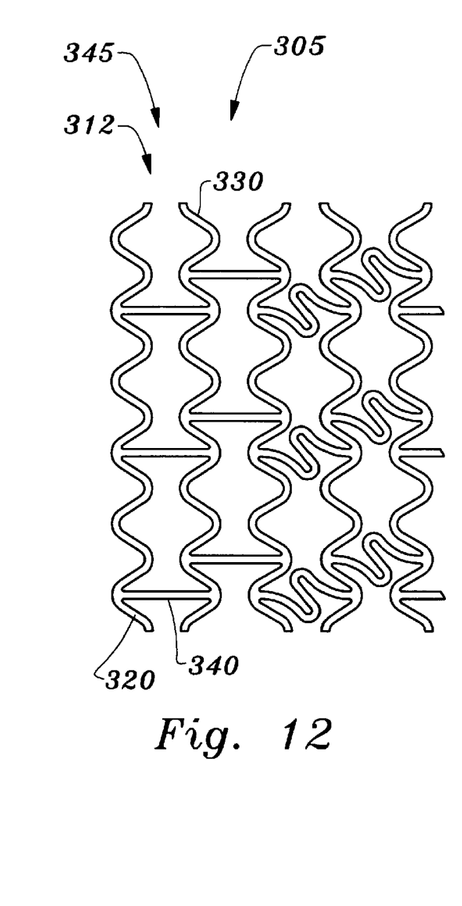
FIG. 12 is a cylindrical projection of a portion of that which is shown in FIG. 1 with a basic marker added to a first end of the stent.
Figure 13:
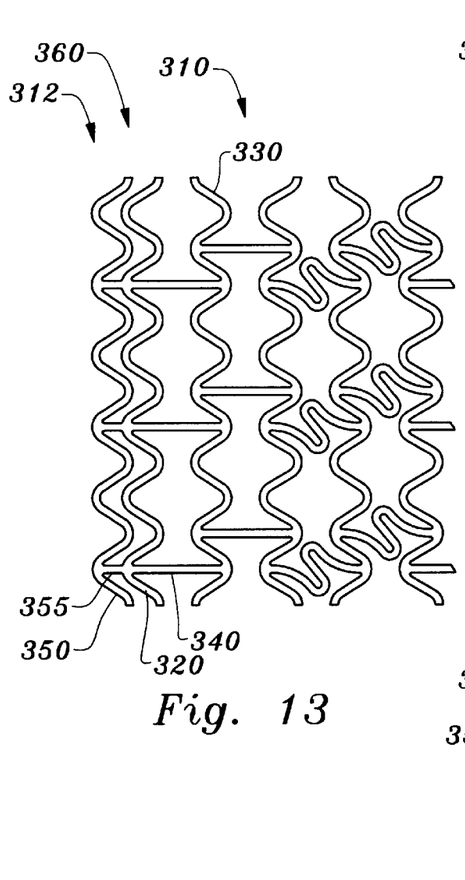
FIG. 13 is a cylindrical projection of a portion of that which is shown in FIG. 1 with an augmented marker attached to a first end of the stent.
Figure 14:
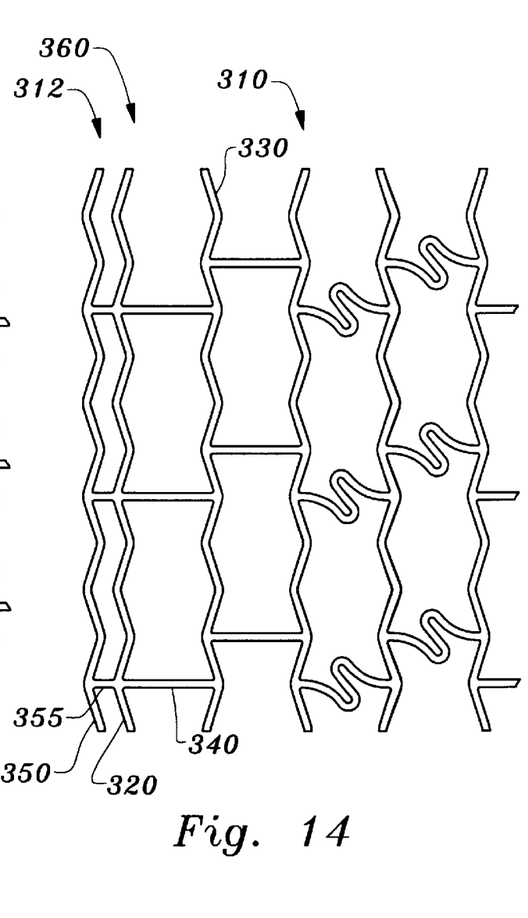
FIG. 14 is a cylindrical projection of that which is shown in FIG. 13 after radial expansion thereof.

With reference to FIGS. 12–14, details of a stent 310 featuring enhanced density markers 360 is described. With reference to FIG. 12, before the enhanced density marker 360 (FIGS. 13 and 14) is added to the stent 305, the stent 305 is configured similarly to the stent 10 of the preferred embodiment (FIG. 1). The first end 312 includes an end element 320 joined to an adjacent transition element 330 by a first link 340. No enhanced density is provided for the stent 305 and hence no enhanced visibility exists for the stent 305. However, the first linear link 340 can be shortened until crests of the end element 320 and transition element 330 are nearly abutting each other.

By shortening the first linear link 340 and bringing the end element 320 closer to the transition element 330, the density of the stent 305 adjacent the first end 312 can be slightly increased to slightly increase the visibility of the end of the stent on a medical imaging device. In essence, a slightly enhanced density marker 345 would be provided adjacent the first end 312 of the stent 305. In a similar fashion, tie bars 51 near a midpoint or other location on the stent 10 of the preferred embodiment can be replaced with shortened first linear links 340 so that a slightly enhanced density marker similar to the slightly enhanced density marker 345 can be provided near a midpoint or other location on the stent 305.

With reference to FIG. 11, details of the preferred enhanced density marker 360 are provided. An in-phase element 350 is oriented beyond the first end 312 of the stent 310. The in-phase element 350 is attached to the end element 320 by a second linear link 355. Because the in-phase element 350 is in-phase with bends in the end element 320, the in-phase element 350 can be located closer to the end element 320 than would otherwise be the case with out of phase elements. Because the in-phase element 350 is so close to the end element 320, a localized density of material forming the stent 310 is significantly enhanced adjacent the first end 312. Thus, the enhanced density marker 360 is provided adjacent the first end 312. With this added density of material, the visibility of the stent 310, at the first end 312 thereof is enhanced when the stent is viewed with a medical imaging device. The in-phase element 350 is provided from a similar material, with a similar number of bends and a similar wave-length and amplitude as the end element 320, so that the in-phase element 350 can be radially expanded along with the end element 320 and other portions of the stent 310 (FIG. 14).

If further augmenting of the enhanced density marker 360 is desired, additional in-phase elements 350 can be located on a side of the in-phase element 350 opposite the end element 320. With each additional in-phase element 350 the density and hence the visibility of the enhanced density marker 360 is augmented.

If the enhanced density marker 360 is to be located at a midpoint or other points spaced from ends of the stent 310, a circumferential element adjacent where the marker 360 is desired is removed from the stent 310 and replaced with an assembly of elements configured similarly to the end element 320, the in-phase element 350 and the second linear link 355. This substitution of a standard circumferential element with a combination of the end element 320 and the in-phase element 350 allows gaps 40 on either side of the removed circumferential element to remain unchanged and allows axial elements 50 to attach to either the end element 320 or the in-phase element 350, depending on the side of the removed circumferential element 20 that the axial element 50 is located. Similarly, additional in-phase elements can be located adjacent the in-phase element 350 at midpoints or other locations between ends of the stent 310 to further augment the density provided by the enhanced density marker 360 at a midpoint of the stent.

This disclosure is provided to reveal a preferred embodiment of the invention and a best mode for practicing the invention. Having thus described the invention in this way, it should be apparent that various different modifications can be made to the preferred embodiment without departing from the scope and fair meaning of this disclosure. When structures are identified as a means to perform a function, the identification is intended to include all structures which can perform the function specified.

What is claimed is:

1. An axially non-contracting flexible surgical stent which is radially expandable from a first compressed diameter to a second larger expanded diameter, the stent comprising in combination:

at least two circumferential elements including a first circumferential element and a second circumferential element, said circumferential elements axially spaced from each by a gap there between;

said at least two circumferential elements circumscribing a central axis of said stent;

said at least two circumferential elements including a wave-like series of bends therein as each said circumferential element circumscribes said central axis of said stent;

each said bend including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;

said bends of said first circumferential element oriented out of phase with said bends of said second circumferential element;

at least one axial element spanning said gap and joining said first circumferential element to said second circumferential element;

said at least one axial element attached to said first circumferential element at a first tip located at one of said troughs and attached to said second circumferential element at a second tip located at one of said troughs;

said at least one axial element including a means to adjust in length axially between said first tip and said second tip, such that said central axis of said stent can flex by having said axial element adjust in length axially;

wherein said length adjustment means of said at least one axial element includes at least one curve in said at least one axial element between said first tip and said second tip, said at least one curve capable of altering a radius of curvature thereof to alter a distance between said first tip and said second tip; and wherein said length adjustment means includes at least two curves located in said at least one axial element between said first tip and said second tip, said two curves curving in opposite directions, each of said at least two curves capable of adjusting radii of curvature thereof such that a distance between said first tip and said second tip can be adjusted.

2. The stent of claim 1 wherein said at least one axial element includes a first curve and a second curve, said first curve spaced from said first tip by a first leg, said second curve spaced from said first curve by a second leg, said second curve spaced from said second tip by a third leg, said first curve located closer to said second tip than said second curve and said second curve located closer to said first tip than said first curve.

3. An axially non-contracting flexible surgical stent which is radially expandable from a first compressed diameter to a second larger expanded diameter, the stent comprising in combination:

at least two circumferential elements including a first circumferential element and a second circumferential element, said circumferential elements axially spaced from each by a gap there between;

said at least two circumferential elements circumscribing a central axis of said stent;

said at least two circumferential elements including a wave-like series of bends therein as each said circumferential element circumscribes said central axis of said stent;

each said bend including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;

said bends of said first circumferential element oriented out of phase with said bends of said second circumferential element;

at least one axial element spanning said gap and joining said first circumferential element to said second circumferential element;

said at least one axial element attached to said first circumferential element at a first tip located at one of said troughs and attached to said second circumferential element at a second tip located at one of said troughs;

said at least one axial element including a means to adjust in length axially between said first tip and said second tip, such that said central axis of said stent can flex by having said axial element adjust in length axially;

wherein said stent includes a series of circumferential elements oriented in separate planes spaced from each other by gaps there between from a first end of said stent to a second end of said stent, a majority of said circumferential elements having said bends out of phase with said bends of adjacent said circumferential elements, such that said gaps have a non-uniform axial width;

wherein at least one adjacent pair of said circumferential elements have one of said gaps there between is spanned by at least one substantially linear tie bar, said tie bar having a first junction at one end of said tie bar and a second junction at the other end of said tie bar, each said junction attached to an opposite one of said pair of said circumferential elements at one of said troughs;

wherein each of said gaps is spanned only by structures which attach to said circumferential elements within troughs;

wherein each said gap spanned by at least one of said axial elements including a means to adjust in length axially is spanned only by said axial elements including a means to adjust in length axially;

wherein each said gap spanned by at least one of said tie bars is spanned only by said tie bars; and wherein said gaps spanned by said tie bars and said gaps spanned by said axial elements including a means to adjust in length axially are each arranged in groups of at least two adjacent gaps spanned by similar structures.

4. The stent of claim 3 wherein said length adjustment means of said at least one axial element includes a first curve and a second curve, said first curve spaced from said first tip by a first leg, said second curve spaced from said first curve by a second leg, said second curve spaced from said second tip by a third leg, said first curve located closer to said second tip than said second curve and said second curve located closer to said first tip than said first curve.

5. A radially expandable surgical stent comprising in combination:
- a series of circumferential elements circumscribing a central axis of said stent, each said circumferential element located in a separate plane spaced axially from adjacent circumferential elements by gaps;
- each said circumferential element having a wave-like series of bends therein as each said circumferential element circumscribes said cylindrical contour of said stent;
- each said bend including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;
- at least one of said gaps spanned by at least one flexible link attached to a trough of each said circumferential element adjacent said gap;
- wherein said flexible link includes at least one curve and at least two legs on opposite sides of said at least one curve, said curve being bendable to adjust a radius of curvature thereof and adjust a length of said flexible link, such that said stent can bend; and
- wherein said flexible link includes a first leg located between a first tip of said flexible link and a first curve, a second link located between said first curve and a second curve and a third leg located between said second curve and a second tip of said flexible link.

6. The surgical stent of claim 5 wherein said first tip and said second tip extend initially substantially axially away from said troughs of said circumferential elements adjacent said gap where said flexible link is located, said flexible link having a width adjacent said first tip and adjacent said second tip which is less than a width of said troughs in said circumferential elements adjacent said gap, such that said first tip and said second tip can extend into said troughs without touching said circumferential elements until said flexible link terminates at said first tip and said second tip where said flexible link joins with said circumferential elements adjacent said gap.

7. A radially expandable surgical stent comprising in combination:
- a series of circumferential elements circumscribing a central axis of said stent, each said circumferential element located in a separate plane spaced axially from adjacent circumferential elements by gaps;
- each said circumferential element having a wave-like series of bends therein as each said circumferential element circumscribes said cylindrical contour of said stent;
- each said bend including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;
- at least one of said gaps spanned by at least one flexible link attached to a trough of each said circumferential element adjacent said gap;
- wherein at least one of said gaps is spanned by at least one of said flexible links extending between crests of said adjacent circumferential elements, each of said crests of said adjacent circumferential elements aligned axially with each other, such that a first tip of said flexible link and a second tip of said flexible link are axially aligned with each other; and
- wherein said flexible links spanning said gaps in a trough-to-trough fashion are axially aligned with flexible links spanning said gaps in a crest-to-crest fashion.

8. A radially expandable surgical stent for implantation into a body lumen such as an artery, and featuring enhanced visibility when viewed by an imaging device, the stent comprising in combination:
- a series of axially spaced circumferential elements, each said circumferential element forming an elongate circuit completely circumscribing said stent, said circumferential elements having a wave-like series of bends therein as each said circumferential element circumscribes said stent, each said bend including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element, said bends of said circumferential elements out of phase with adjacent circumferential elements;
- at least one in-phase element located adjacent at least one of said circumferential elements, said in-phase element having a contour similar to that of said adjacent one of said circumferential elements; and
- at least one axial element joining said in-phase element to said adjacent circumferential element, said axial element having a length sufficiently short to locate said in-phase element closer to said adjacent circumferential element than a spacing between other adjacent said circumferential elements, such that a visibility of said adjacent circumferential element and said in-phase element together is greater than a visibility pf pairs of said circumferential elements when viewed by an imaging device.

9. The stent of claim 8 wherein said axial element is substantially linear.

10. The stent of claim 8 wherein said in-phase element is located near a middle of said stent.

11. The stent of claim 10 wherein said stent includes in-phase elements adjacent first and second ends of said stent.

* * * * *